US005692900A

United States Patent [19]
Fischer

[11] Patent Number: 5,692,900
[45] Date of Patent: *Dec. 2, 1997

[54] PATIENT DENTIST WHITENING GUIDE

[75] Inventor: Dan E. Fischer, Sandy, Utah

[73] Assignee: Ultradent Products, Inc., South Jordan, Utah

[*] Notice: The term of this patent shall not extend beyond the expiration date of Pat. No. 5,685,712.

[21] Appl. No.: 734,106

[22] Filed: Oct. 21, 1996

Related U.S. Application Data

[63] Continuation of Ser. No. 474,447, Jun. 7, 1995, abandoned.

[51] Int. Cl.$^6$ ............................................. A61C 19/10
[52] U.S. Cl. ............................................. 433/26
[58] Field of Search ............................................. 433/26

[56] References Cited

U.S. PATENT DOCUMENTS

| | | | |
|---|---|---|---|
| 4,744,378 | 5/1988 | Bostic | 433/26 |
| 4,919,617 | 4/1990 | Antons et al. | 433/26 |
| 5,149,267 | 9/1992 | Longhini et al. | 433/26 |
| 5,261,815 | 11/1993 | Pozzi | 433/26 |
| 5,588,834 | 12/1996 | Resk et al. | 433/26 |

*Primary Examiner*—Edgar S. Burr
*Assistant Examiner*—Daniel J. Colilla
*Attorney, Agent, or Firm*—Workman Nydegger Seeley

[57] ABSTRACT

A tooth shade whitening guide formed from a flat, thin body member and having a patient portion and a separable dentist portion. The patient portion and the dentist portion each having a front face with a plurality of distinct tooth color samples positioned thereon. Indicia is positioned adjacent to each of the distinct tooth color samples identifying the corresponding tooth color shade. The indicia includes a first set of indicia and a second set of indicia. The first set of indicia is positioned in a forward configuration so as to be readable in a standard fashion. The second set of indicia is printed in a backward configuration so as to be readable in a conventional forward orientation when viewed in a mirror. The patient portion further has a plurality of display tabs projecting therefrom. The distinct tooth color samples are disposed over top of the display tabs for comparison with the patient's teeth.

8 Claims, 3 Drawing Sheets

PATIENT DENTIST WHITENING GUIDE

This application is a continuation of application Ser. No. 08/474,447, filed Jun. 7, 1995, now abandoned.

BACKGROUND OF THE INVENTION

1. The Field of the Invention

This invention relates generally to dental tooth shade guides and more specifically to tooth shade whitening guides usable by both a dentist and a patient.

2. The Relevant Technology

Early in the history of dentistry, dental restoration devices such as caps, individual replacement teeth, or complete sets of dentures could only be made in a limited number of shades of white. Since the patient had a minimal choice as to color, there was little need to accurately identify a patient's tooth color. As dentistry progressed, however, it became possible to manufacturing dental restoration devices having any desired color or shade. With this evolution came the need to precisely identify a patient's tooth color so that color of the dental restoration device made for the patient would match the patient's natural tooth color.

To facilitate the matching of tooth color, a number of tooth color shade guides have been developed. Such guides typically comprise some form of structure on which an array to tooth color samples are positioned. During use, a dentist or other dental professional compares the color shades on the guide to the patient's teeth to identify the color shade closest to the color of the patient's teeth. Over the years, an industry standard for tooth shades has developed which encompasses the majority of human tooth shades. It is thus possible for the dental professional to obtain an extremely precise match by comparing a patient's tooth color to the full array of standardized tooth color samples.

To facilitate the color comparison, tooth color shade guides usually include a number of separate or separable guides each having a distinct tooth color sample disposed thereon. In this way, the dental professional can individually view and compare a selected color shade against a patient's tooth. Each separate guide typically also has the industry standard alpha-numeric characters assigned to the hue of the tooth color sample disposed thereon. This facilitates the dental professionals proper identification of the tooth color sample which most closely matches the patient's tooth color.

As can be appreciated, as precise a match as possible is desired since the dental restoration device to be produced will become a permanent or semi-permanent part of the patient's denture. Therefore, much attention has been placed on providing tooth color shade guides which allow for as precise an identification as possible.

Both disposable and non-disposable color shade guides are manufactured. Non-disposable tooth color shade guides must be made so as to be sterilizable. This is to prevent contamination from one patient to the next. Some non-disposable tooth color shade guides are made from metal strips on which reside the various specimens. Alternatively, glass rods have been used on which are disposed the specimens.

In the case of disposable tooth color shade guides, some methods have been provided for identifying when the color shade guide has been used and is, thus, contaminated. Such methods include the use of special paper that changes color by reacting to saliva or light once the tooth color shade guide has been used.

As dentistry has progressed, new methods and compounds have allowed dentists to effectively alter a patient's tooth color. Typically, a patient will desire to whiten their teeth. With proper treatment, a whitening effect can slowly be achieved over time.

As a part of this treatment, it is advantageous to monitor a patient's tooth color. Such monitoring requires a general identification of a patient's tooth color for purposes of modifying treatment. It is further advantageous for this monitoring to occur on a frequent basis, typically more frequently than a patient or dental professional would like to schedule office visits.

Although conventional tooth color shade guides could be used to monitor the tooth whitening process, these conventional guides are relatively expensive and difficult for a patient to independently use. As previously discussed, conventional tooth color shade guides include a large variety of tooth color samples so as to enable an exact match with the patient's tooth color. The large number of colors increases the cost of the conventional guides. Non-disposable guides have increased manufacturing costs and are clearly prohibitively expensive when considering distribution to each patient. Conventional disposable guides are also prohibitively expensive since a patient must frequently monitor the shade of their teeth during the whitening process.

Conventional tooth shade guides are also designed so as to require the dentist to compare the tooth color samples on the guide to the patient's tooth color. Since the patient's tooth color must frequently be monitored during the whitening process, use of conventional tooth shade guide can be expensive, time consuming, and inconvenient when considering the large number of dental office visits required.

Another difficulty with tooth shade guides found in the prior art is that they tend to be relatively difficult for a patient to use for purposes of self-examination of his or her teeth.

OBJECTS AND SUMMARY OF THE INVENTION

Thus, what is needed is an improved tooth color shade guide that is simple and inexpensive to manufacture and that is simple and easy in use for patient self-examination. Accordingly, it is an object of the present invention to provide improved tooth color shade guides for monitoring the tooth color of a patient.

It is also and object of the present invention to provide improved tooth color shade guides that are relatively inexpensive.

It is also another object of the present invention to provide improved tooth color shade guides that enable a patient to independently monitor the tooth color of the patient's teeth.

Still another object of the present invention is to provide improved tooth color shade guides that can be used for monitoring the tooth color of a patient without requiring the patient to visit the dentist.

Yet another object of the present invention is to provide an improved tooth color shade guide that is easy to use by a patient for self-examination.

Finally, it is an object of the present invention to provide improved tooth color shade guides that can be repeatedly used by a patient.

These and other objects and features of the present invention will become more fully apparent from the following description and appended claims, or may be learned by the practice of the invention as set forth hereinafter.

To achieve the foregoing objects, and in accordance with the invention as embodied and broadly described herein, a tooth shade whitening guide is provided for patient and dentist identification of the color shade of the teeth of the patient. The whitening guide comprises a flat, thin body member having a pair of separable portions. One of the pair of separable portions includes a patient portion. The patient portion has a front side, an opposing back side, an outer edge, and an opposing inner edge. A plurality of display tabs project from the outer edge of the patient portion. The plurality of display tabs define a plurality of notches individually disposed between each of the display tabs.

A first set of distinct tooth color samples individually overlie each of the display tabs on the front side of the patient portion. The tooth color samples preferably correspond to an industry standard tooth shade. Indicia is positioned adjacent to each of the first set of distinct tooth color samples identifying each of the tooth color samples. The indicia is printed in a forward configuration and a backward configuration. The backward configuration is readable in a standard forward orientation when viewed in a reflection of a mirror. This occurs as the patient compares by reflection in the mirror the distinct tooth color samples on the patient portion to the teeth of the patient positioned adjacent to the whitening guide.

The guide also includes a dentist portion separably attached to the patient portion. The dentist portion also includes a front side, an opposing back side, an outer edge, and an opposing inner edge. A second set of distinct tooth color samples are positioned on the front side of the dentist portion and correspond to the first set of distinct tooth color samples. In a similar fashion, indicia can be placed on the dentist portion adjacent to the second set of distinct tooth color samples. The indicia on the dentist portion can be positioned in both a forward configuration and a backward configuration as previously discussed.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
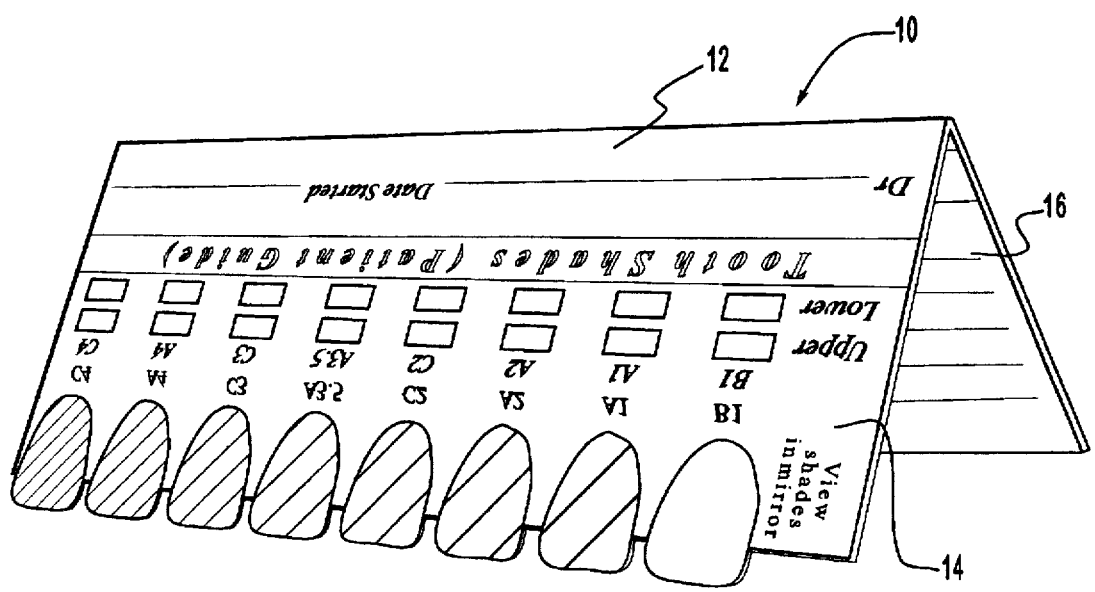
FIG. 1 is a perspective view of an inventive patient/dentist whitening guide showing the guide partially folded along a line separating a patient portion from a dentist portion.

Disclosed in FIG. 1 is a perspective view of one embodiment of a tooth whitening guide 10 incorporating features of the present invention. As disclosed therein, tooth whitening guide 10 is formed of a flat, thin body member 12 comprising a patient portion 14 and an integrally attached dentist portion 16. Body member 12 is preferably made from conventional card or paper stock but can also be made from sheets of plastic or other materials.

Figure 2:
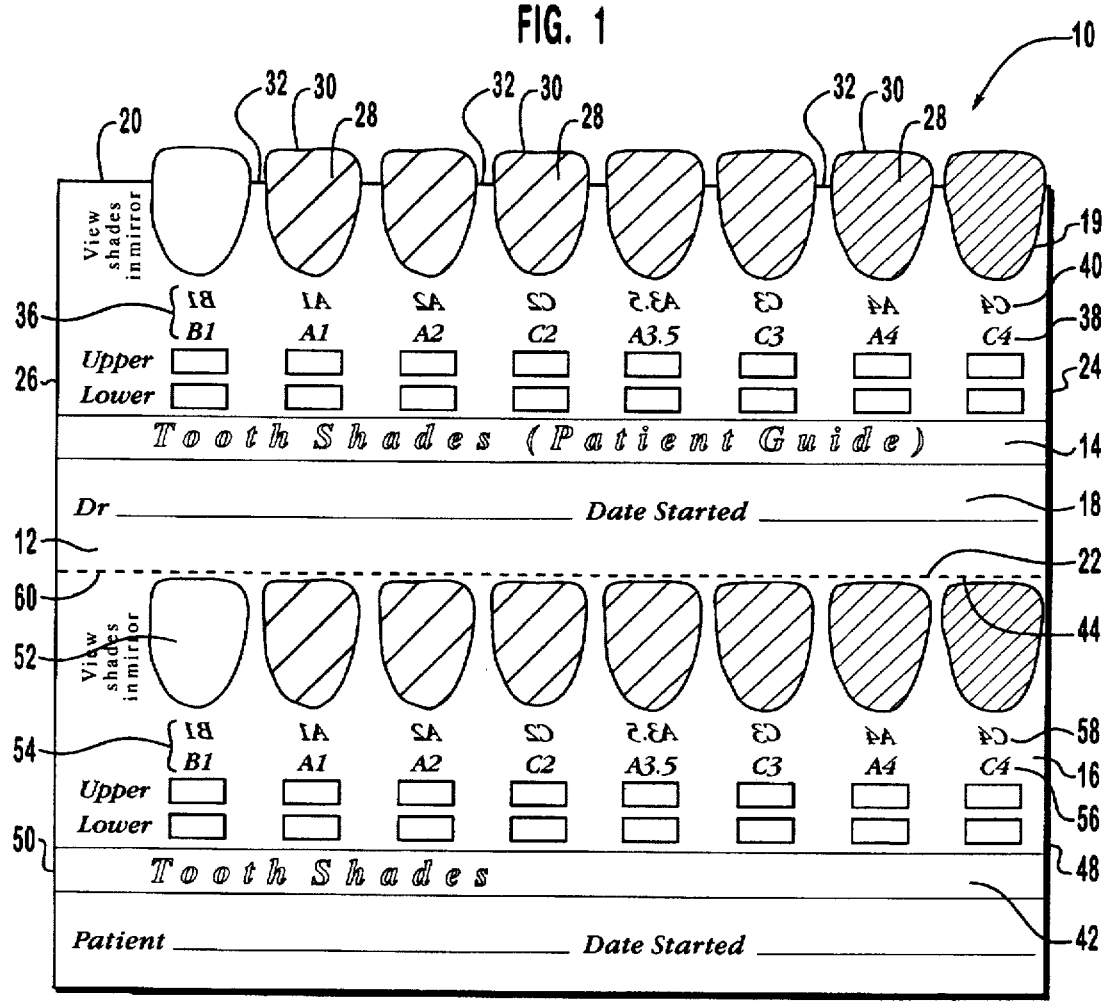
FIG. 2 is a front plan view of the inventive patient/dentist whitening guide shown in FIG. 1.

FIG. 2 discloses patient portion 14 as having a front face 18 defined by an outer edge 20, an opposing inner edge 22, and a pair of opposing side edges 24 and 26. Outwardly projecting from outer edge 20 on a plane parallel to front face 18 are a plurality of display tabs 28. Display tabs 28 are integrally and rigidly secured to patient portion 14. Each of display tabs 28 have a free edge 30 which define a plurality of notches 32 individually disposed between each of display members 28.

Disposed on front face 18 so as to individually cover display members 28 and an adjacent section 19 of patient portion 14 are a plurality of distinct tooth color samples 34. Tooth color samples 34 preferably correspond to standardized tooth color shades, such as Vita shades. Tooth whitening guide 10 is not used to precisely identify the tooth color shade of a patient's teeth but rather to generally identify the whitening of the patient's teeth. Accordingly, although any number of color shades can be used, the preferred embodiment uses between six to ten individual color shades. The color shades preferably cover a relatively large range of colors. By minimizing the number of tooth color samples 34 on tooth whitening guide 10, tooth whitening guide 10 becomes smaller, less expensive, and easier to handle than conventional tooth color shade guides.

As will be discussed later with reference to use of the tooth whitening guide 10, one of the benefits of positioning tooth color samples 34 over display tabs 28 having notches 32 disposed therebetween is that a clearer comparison can be made between the teeth of a patient and one of selected tooth coloring shades 34. The configuration of tooth color samples 34 also allows a portion of individual tooth color samples 34 to be selectively positioned immediately adjacent to the patient's teeth for ease of comparison.

A set of printed indicia 36 are positioned adjacent to teeth color samples 34 on front face 18, identifying each of tooth color samples 34. Indicia 36 preferably correspond to standardized tooth color shade designations. Indicia 36 comprises a first set of indicia 38 and a second set of indicia 40. First set of indicia 38 is oriented in a forward configuration so as to be readable in a standard fashion. In contrast, second set of indicia 40 are positioned in a backward configuration so as to be readable in a conventional forward orientation when viewed in a reflection of a mirror.

As also disclosed in FIG. 2, dentist portion 16 comprises a front face 42 that is bounded by an inner edge 44, an outer edge 46, and opposing side edges 48 and 50. Disposed on front face 42 of dentist portion 16 is a second set of distinct tooth color samples 52. Second set of distinct tooth color samples 52 correspond to distinct tooth color samples 34 on patient portion 14 and are consecutively positioned adjacent to inner edge 44. In an alternative embodiment, second set of distinct tooth color samples 52 can be positioned anywhere on dentist portion 16.

A set of printed indicia 54 are positioned on dentist portion 16 adjacent to second set of distinct tooth color samples 52, identifying each of tooth color samples 52. Indicia 54 comprises a first set of indicia 56 and a second set of indicia 58. The first set of indicia 56 is oriented in a forward configuration so as to be readable in a standard fashion. In contrast, second set of indicia 58 are positioned in a backward configuration so as to be readable in a conventional forward orientation when viewed in a reflection of a mirror.

Tooth color samples 34 and 52 and all other indicia are preferably printed onto body member 12 using a conventional four to six color offset printing process. Care must be taken to insure that the color of color shades 34 and 52 properly correspond to the identifying indicia. Once the printing is applied, a varnish can be disposed over the printing so as to protect the printing and body member 12.

In one embodiment of the present invention, means are provided for separating patient portion 14 from dentist portion 16. By way of example and not by limitation, perforations 60 are provided where inner edge 22 of patient portion 14 and inner edge 44 of dentist portion 16 intersect. Accordingly, by applying opposing forces between patient portion 14 and dentist portion 16, patient portion 14 and dentist portion 16 can be separated by producing a tear along perforations 60. Alternative embodiments for separating patient portion 14 and dentist portion 16 include any number of different types of hales or creases that can be positioned between patient portion 14 and dentist portion 16 so as to enable separation between patent portion 14 and dentist portion 16.

Figure 3:
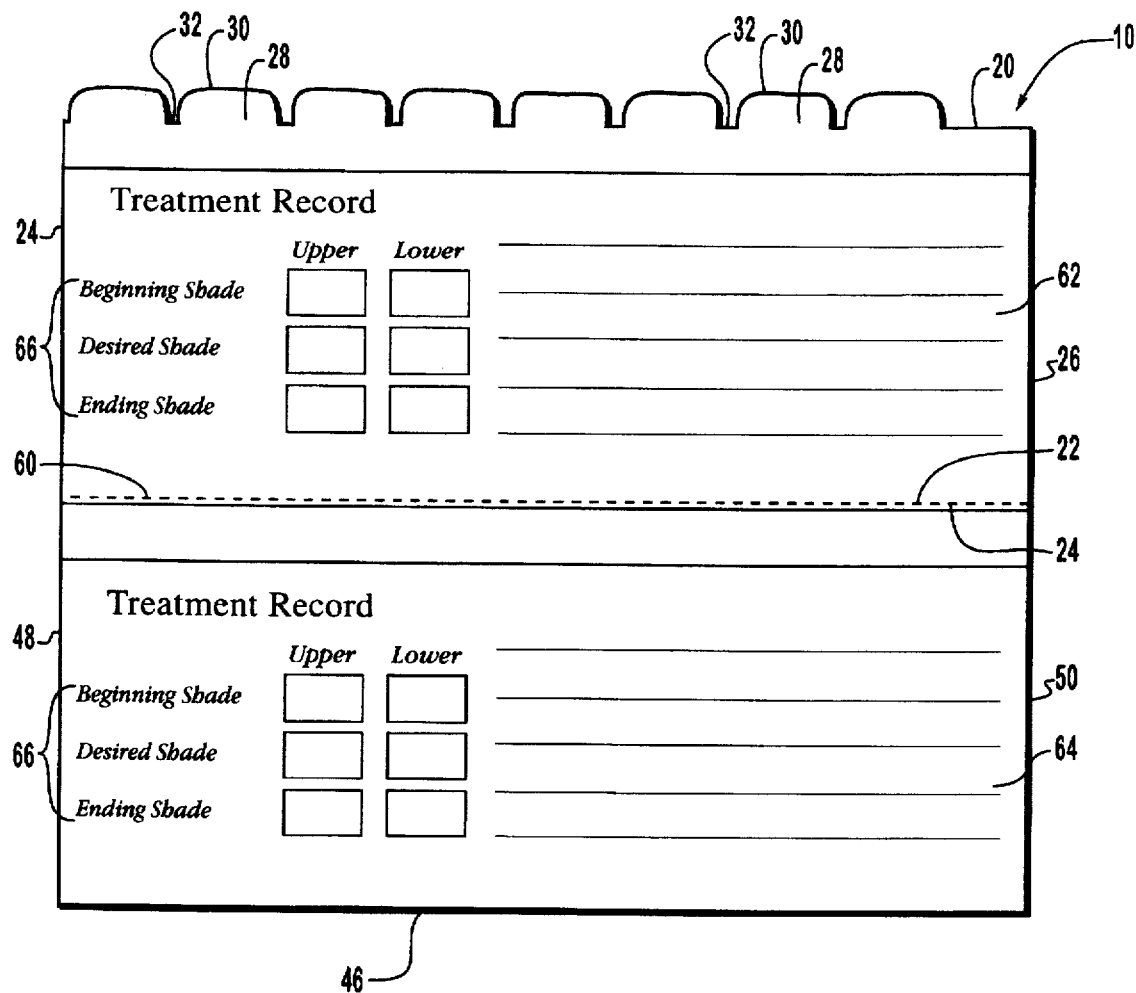
FIG. 3 is a back plan view of the inventive patient/dentist whitening guide shown in FIG. 1.

FIG. 3 discloses patient portion 14 and dentist portion 16 as each having a back side 62 and 64, respectively. Printed on back side 62 and 64 is complementary indicia 66 for outlining treatments and changes in the color shade of the patient's teeth.

Figure 4:
FIG. 4 is a perspective view of the patient portion shown in FIG. 1 being used by a patient to identify the tooth color shade of the teeth of the patient.

During use of tooth whitening guide 10, a dentist will initially determine the beginning shade of a patient's teeth, and record the information on both the patient portion 14 and dentist portion 16. The patient portion 14 and dentist portion 16 are then separated so that the patient is allowed to take the patient portion 14 while the dentist retains the dentist portion 16. Periodically, as the patient continues the treatment for whitening the patient's teeth, the patient will independently use patient portion 14 to identify the shade of the patient's teeth. As shown in FIG. 4, this is accomplished by a patient 68 positioning display tabs 28 having tooth color samples 34 positioned thereon adjacent to a patient's teeth 70. By looking at a reflection 71 in a mirror 72, patient 68 can independently compare tooth color samples 34 against the color of patient's teeth 70, thereby determining tooth shade color 34 closest to the patient's tooth color.

Patient 68 can then read indicia 38 in reflection 71 of mirror 72 to properly identify tooth color sample 34 closest to the patient's tooth color. As previously discussed, indicia 38 is initially printed in a backward configuration so that it is readable in a conventional forward orientation as patient 68 reads indicia 38 in reflection 71 of mirror 72. This information can then be recorded on the patient portion 14 and then conveyed by telephone or other means to the dentist who can record the information on dentist portion 16. With this information, the dentist is able to monitor and vary the tooth whitening treatment as necessary.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A tooth shade whitening guide for use by both a dentist and a patient to identify the color shade of the teeth of the patient when using a home bleaching kit, said whitening guide comprising:
   (a) a dentist portion comprising:
      (i) a flat, thin body member having a front side, an opposing back side and an outer edge;
      (ii) a plurality of distinct tooth color samples consecutively disposed on said front side of said body member adjacent to said outer edge; and
      (iii) indicia positioned adjacent to each of said distinct tooth color samples identifying each of said distinct tooth color samples, said indicia including means for recording an identified tooth shade; and
   (b) a patient portion removable attached to said dentist portion and comprising:
      (i) a flat, thin body member having a front side, an opposing back side and an outer edge;
      (ii) a plurality of distinct tooth color samples consecutively disposed on said front side of said body member adjacent to said outer edge; and
      (iii) indicia positioned adjacent to each of said distinct tooth color samples identifying each of said distinct tooth color samples, said indicia including means for recording an identified tooth shade.

2. A tooth shade whitening guide as recited in claim 1, wherein each said body member further comprises a plurality of display tabs integrally secured to said body member and outwardly projecting from said outer edge of said body member.

3. A tooth shade whitening guide as recited in claim 2, wherein said distinct tooth color samples are also individually disposed on each of said display tabs.

4. A tooth shade whitening guide as recited in claim 1, wherein said distinct tooth color samples correspond to an industry standard tooth shade.

5. A tooth shade whitening guide as recited in claim 1, wherein said indicia on said dentist portion is printed in a forward configuration.

6. A tooth shade whitening guide as recited in claims 1 or 5 wherein said indicia on said patient portion is printed in a backward configuration so as to be readable in a conventional forward orientation when viewed in a mirror as the patient compares by reflection in the mirror said tooth color samples on said patient portion to the patient's teeth.

7. A tooth whitening guide as recited in claim 1, wherein said body member comprises a plurality of perforations disposed through said body member for removing said dentist portion from the patient portion.

8. A tooth whitening guide as recited in claim 6, wherein said body member comprises a plurality of perforations disposed through said body member for removing said dentist portion from the patient portion.

* * * * *

UNITED STATES PATENT AND TRADEMARK OFFICE
CERTIFICATE OF CORRECTION

PATENT NO. : 5,692,900
DATED : December 2, 1997
INVENTOR(S) : Dan E. Fischer

It is certified that error appears in the above-identified patent and that said Letters Patent is hereby corrected as shown below:

Col. 5, line 16, after "of" change "hales" to --holes--

Col. 5, line 41, after "indicia" change "38" to --40--

Col. 5, line 44, before "is" change "38" to --40--

Col. 5, line 46, after "indicia" change "38" to --40--

Signed and Sealed this

Thirtieth Day of June, 1998

Attest:

BRUCE LEHMAN

Attesting Officer　　Commissioner of Patents and Trademarks